United States Patent [19]

Kulin et al.

[11] 4,412,834
[45] Nov. 1, 1983

[54] ANTIMICROBIAL ULTRAVIOLET IRRADIATION OF CONNECTOR FOR CONTINUOUS AMBULATORY PERITONEAL DIALYSIS

[75] Inventors: Ralph Kulin, Marengo, Ill.; Jack W. Moncrief; Robert P. Popovich, both of Austin, Tex.; Ronald C. Stauber, Hawthorne Woods, Ill.

[73] Assignee: Baxter Travenol Laboratories, Deerfield, Ill. ; by said Ralph Kulin and Ronald C. Stauber

[21] Appl. No.: 270,743

[22] Filed: Jun. 5, 1981

[51] Int. Cl.³ .................... A61J 7/00; F16L 35/00
[52] U.S. Cl. ................... 604/29; 604/283; 604/905; 285/3; 137/625.41
[58] Field of Search ............... 128/213, 214, 214.2, 128/214.6, 274, 675; 285/3; 250/455; 222/83; 137/625.41; 604/905, 29, 283, 103

[56] References Cited

U.S. PATENT DOCUMENTS

| | | | |
|---|---|---|---|
| 2,145,196 | 1/1939 | Biggs . | |
| 3,391,951 | 7/1968 | Miller | 285/3 |
| 3,626,938 | 12/1971 | Versaci . | |
| 3,780,736 | 12/1973 | Chen | 137/625.41 X |
| 3,814,680 | 6/1974 | Wood | 210/64 |
| 3,916,950 | 11/1975 | Mongerson et al. | 137/625.41 |
| 3,926,556 | 12/1975 | Boucher | 21/54 |
| 3,955,922 | 5/1976 | Moulthrop | 21/102 |
| 3,957,082 | 5/1976 | Fuson et al. | 128/274 X |
| 3,986,508 | 10/1976 | Barrington | 222/83 X |
| 3,994,686 | 11/1976 | Rauser et al. | 21/102 |
| 4,056,116 | 11/1977 | Carter et al. | 128/214.2 |
| 4,063,890 | 12/1977 | Baron | 21/54 |
| 4,069,153 | 1/1978 | Gunther | 210/64 |
| 4,080,965 | 3/1978 | Phillips . | |
| 4,121,107 | 10/1978 | Bachmann . | |
| 4,141,686 | 2/1979 | Lewis | 250/436 |
| 4,173,234 | 11/1979 | Thomas . | |
| 4,201,917 | 5/1980 | Graentzel | 250/431 |
| 4,219,221 | 8/1980 | Webb . | |
| 4,242,310 | 12/1980 | Greff et al. | 422/300 |
| 4,291,701 | 9/1981 | Bowman | 128/675 |
| 4,346,703 | 8/1982 | Dennehey et al. . | |

OTHER PUBLICATIONS

German article entitled "The sterilization of Medical Plastic Substances by Ultraviolet Rays", Strahlentherapie 111, 626-631 (1960) (English translation).
Abstract by Joshi et al., entitled "In Vitro Studies of Surface Sterilization of Continuous Ambulatory Peritoneal Dialysis Tubing Using Ultraviolet Light", *Kidney International Official Journal of the International Society of Nephrology*, vol. 1, Jan. 1981.
"Frozen Red Cell Outdating", DHEW Publication No. (NIH) 76-1004 dated Mar. 14, 1975.
Eisenger article from *Clinical Nephrology*, vol. 14, No. 1 1980, pp. 42-44.

*Primary Examiner*—Stephen C. Pellogrino
*Attorney, Agent, or Firm*—Paul C. Flattery; Thomas R. Schuman; Garrettson Ellis

[57] ABSTRACT

A connector valve for selectively permitting the transfer of fluids therethrough is described. Multiple-way valve means communicates with a plurality of conduits and selectively permits and prevents flow between the conduits. The multiple-way valve means comprises outer walls made of a substantially ultraviolet-transmissive material, with the outer walls of the multiple-way valve means preferably enclosing an elastomeric seal member defining rotatable channel means for communication with differing conduits at differing rotational positions, and also providing a rotatable seal against inner surfaces of the outer walls to maintain an antimicrobial seal of said conduits. The channel means is exposed along its entire length to an inner surface of an outer wall, to facilitate the antimicrobial effect of ultraviolet radiation. Also, a novel method of practicing continuous ambulatory peritoneal dialysis, and an ultraviolet light applicator, is disclosed.

34 Claims, 13 Drawing Figures

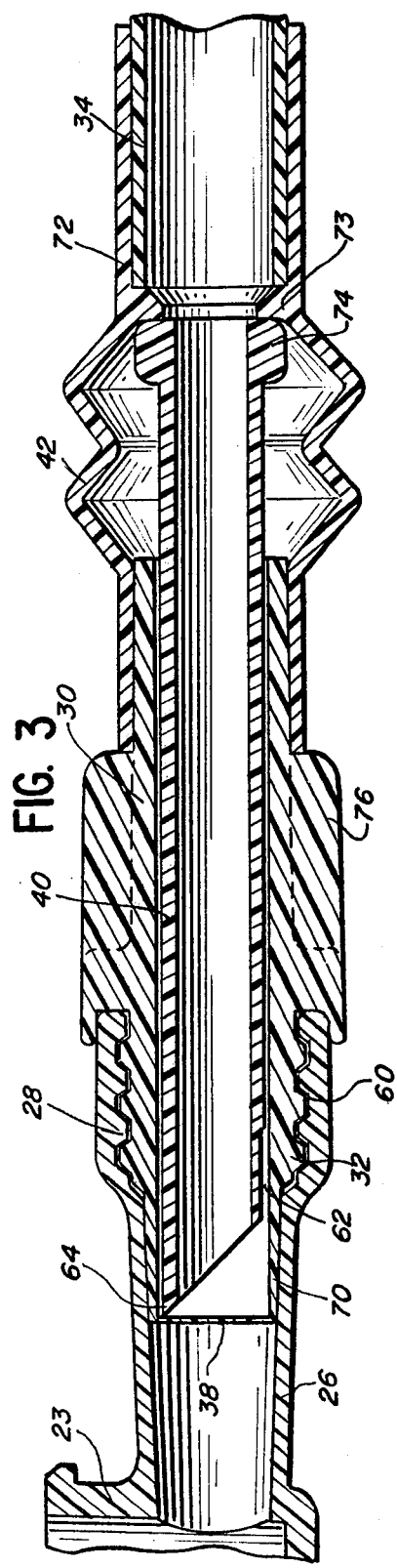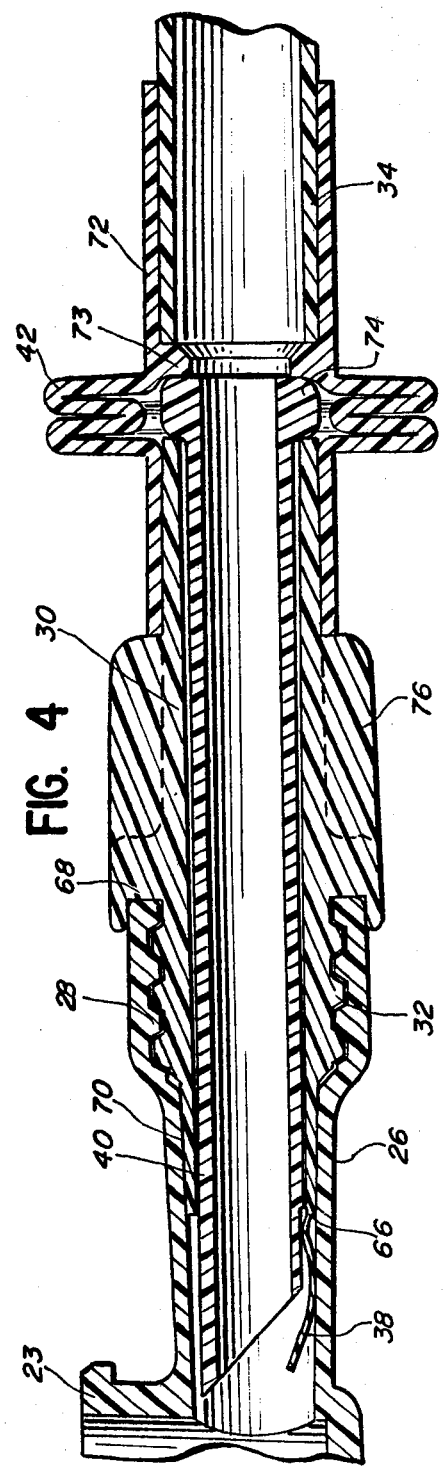

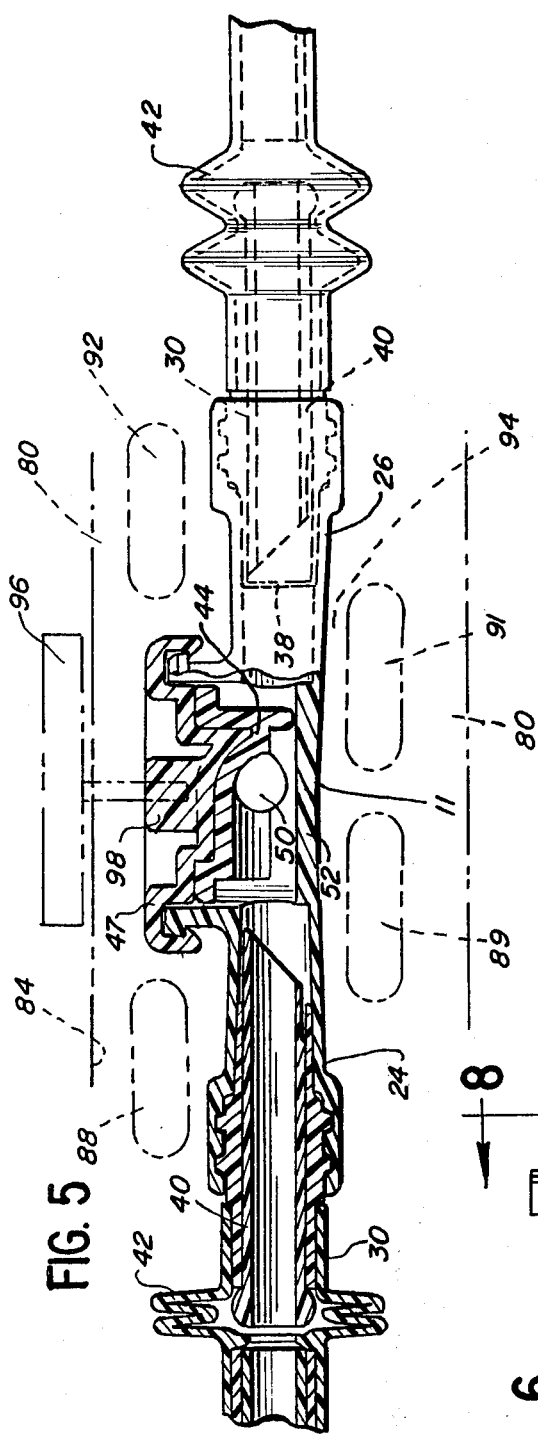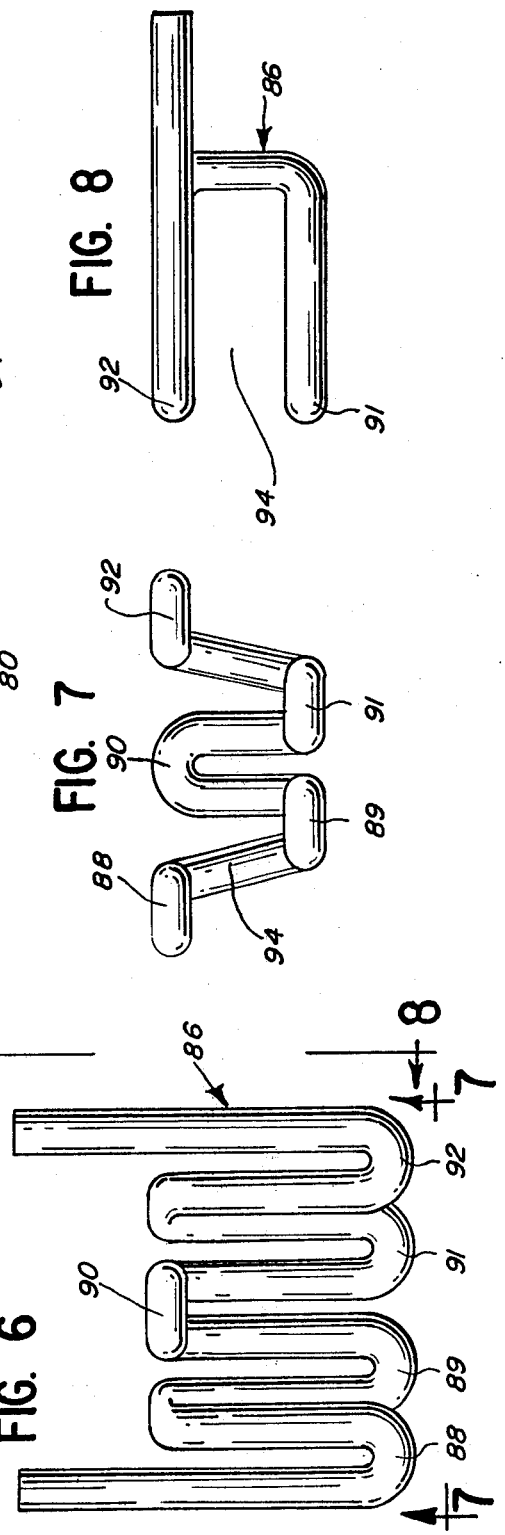

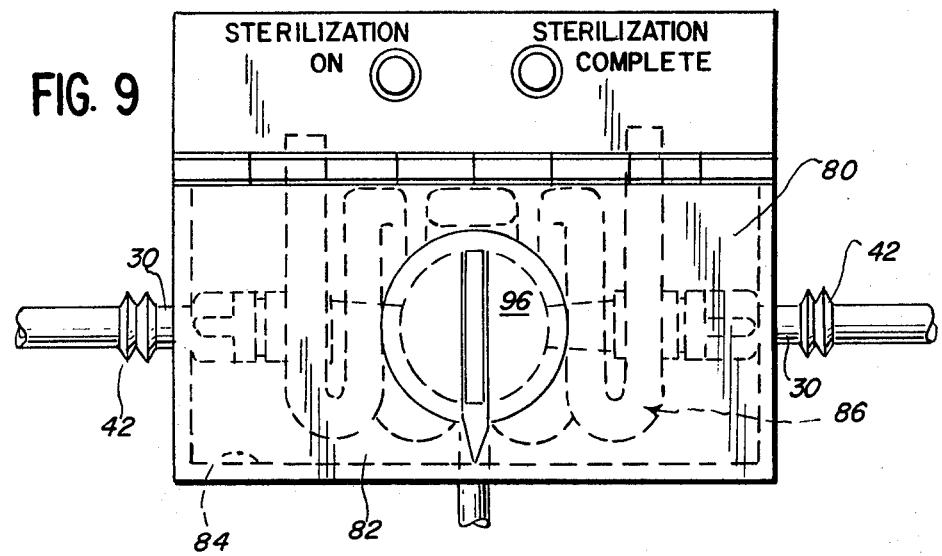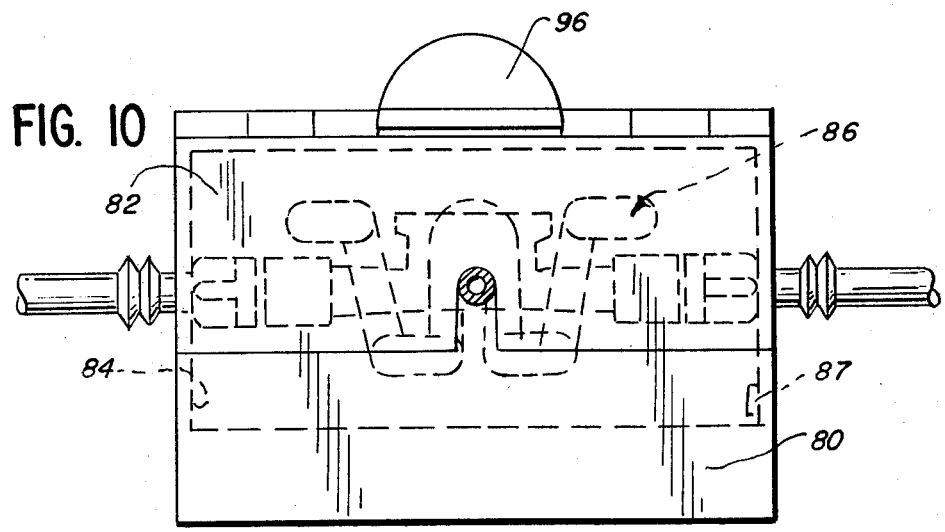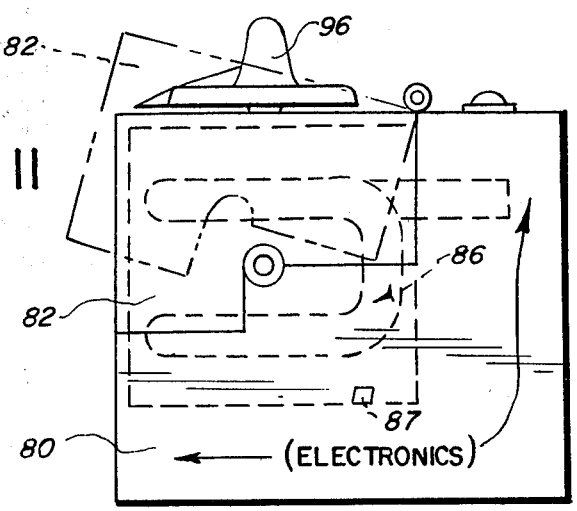

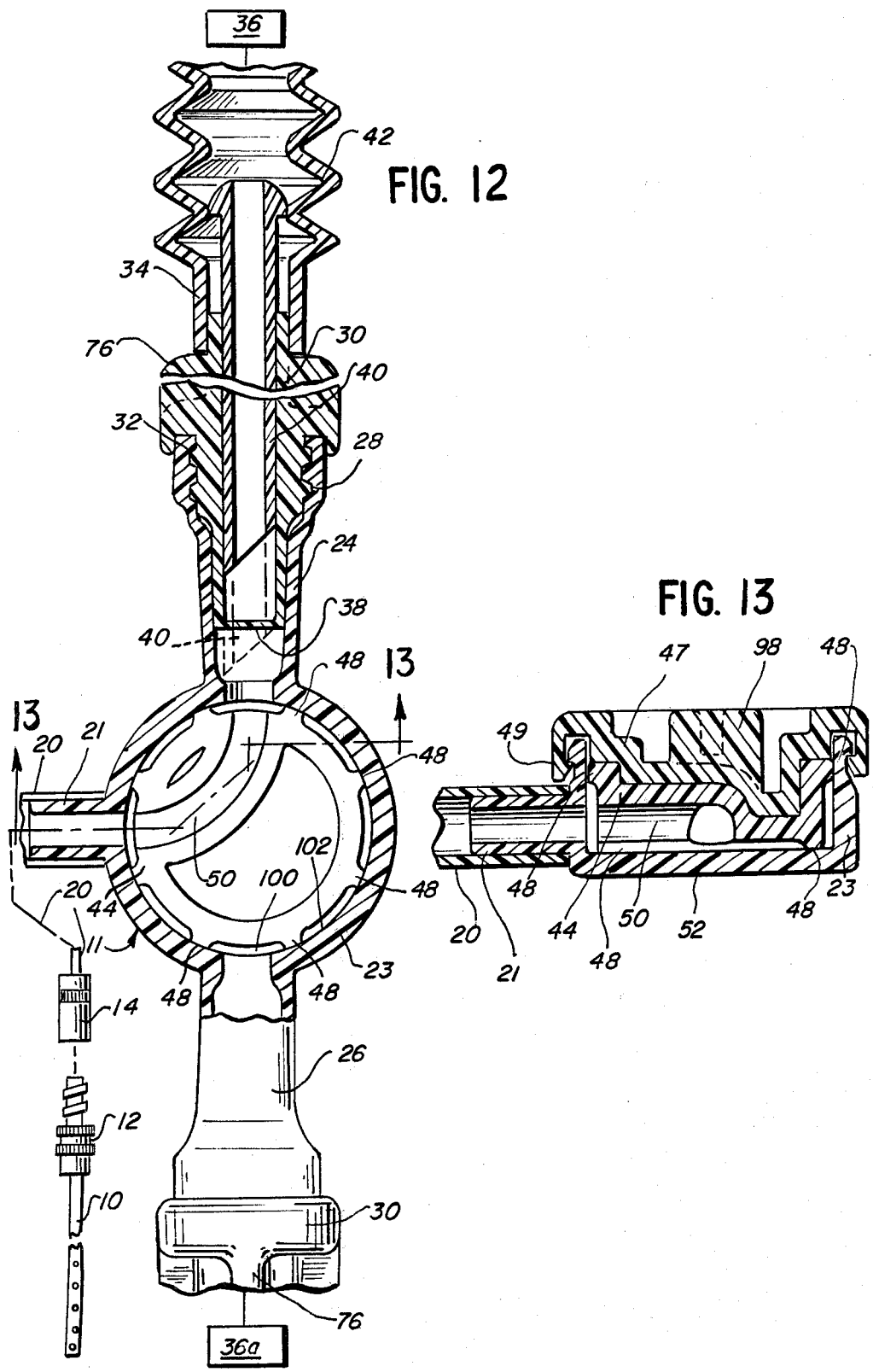

ANTIMICROBIAL ULTRAVIOLET IRRADIATION OF CONNECTOR FOR CONTINUOUS AMBULATORY PERITONEAL DIALYSIS

BACKGROUND OF THE INVENTION

The recently developed technique of continuous ambulatory peritoneal dialysis (CAPD) to remove impurities from the blood of a patient whose kidneys have failed permits the patient being dialyzed to carry a surgically implanted catheter which may be connected intermittently to a peritoneal dialysis transfer set. The transfer set, in turn, connects to a bag of peritoneal dialysis solution, which is emptied through the transfer set into the peritoneal cavity (CAPD infusion phase). The patient is not "tied" to a machine and can be ambulatory while the dialysis across the peritoneal membrane (CAPD dwell phase) takes place. After the dwell phase, the peritoneal dialysis solution is drained (CAPD drain phase) from the peritoneal cavity. This can be done by allowing the solution to flow back into the bag; there is perferably no disconnection of the bag during the dwell phase. After the drain phase, the bag with spent peritoneal dialysis solution may be disconnected from the transfer set and discarded.

A description of the continuous ambulatory peritoneal dialysis technique may be found in Popovich et al. U.S. Pat. No. 4,239,041, issued Dec. 16, 1980 and entitled "METHOD FOR CONTINUOUS AMBULATORY PERITONEAL DIALYSIS".

It is important to make the connections and disconnections of the bags of fresh and spent peritoneal dialysis solution in an aseptic manner, since patients undergoing peritoneal dialysis risk developing peritonitis, an infection which is relatively difficult to control. The risk of bacterial or other microbial contamination of the peritoneal dialysis system is of course increased at the time when the connections and disconnections of the solution containers to the tubing are made. In the event of bacterial contamination, the bacteria can migrate into the peritoneal cavity.

In Barrington U.S. Pat. No. 3,986,508, it is proposed that medical connector members may be sterilized after their connection, for example, with ultraviolet radiation.

By the invention of this application, a method and apparatus are provided for repeatedly or continuously providing an antimicrobial effect on the connection junctions of tubing communicating between the above-described catheter and connected solution container, with any contaminating bacteria being isolated in restricted areas after the connection is made. Antimicrobial effect in these areas is accomplished by ultraviolet radiation. Thereafter, inner seals may be opened so that the system may be used to transfer solution from a container to the peritoneal cavity of a patient.

SUMMARY OF THE INVENTION

In this invention, a connector valve is provided for selectively permitting the transfer of fluids therethrough. The connector valve comprises multiple-way valve means, for example a three-way valve, communicating with a plurality of conduits and selectively permitting and preventing flow between the conduits. One of the conduits may communicate with a catheter leading to the peritoneal cavity of the patient, while the other conduits may be selectively connected to containers for providing or receiving fresh or spent peritoneal dialysis solution.

The multiple-way valve means comprises outer walls made of substantially ultraviolet-transmissive material, and preferably enclosing an elastomeric seal member. The seal member defines a rotatable flow channel means for communication with different conduits at different rotational positions, and provides rotatable seal means against inner surfaces of the outer walls to maintain antimicrobial conditions within the valve.

The flow channel means is exposed along its entire length to an inner surface of an outer wall, so that the surfaces defining the flow channel means can receive the antimicrobial effect of ultraviolet radiation passing through these surfaces. Also, means are provided for rotating the seal member relative to the conduits for operation of the valve.

In is generally preferable for one or more of the conduits to carry at their ends threaded means for receiving and fixedly retaining couplers connected to the fluid containers (hereafter called "bags"). These couplers may project into the threaded conduits, preferably to provide a sealing luer-type connection with the conduits in addition to the threaded connection.

The couplers also have frangible means preventing flow through the couplers; the frangible means are openable to permit flow without disconnection from the conduits, with the outer surfaces of the couplers positioned within the conduits to receive the antimicrobial effect of ultraviolet light passing through the valve means.

Thus, a connection may be made between the threaded conduits and the coupler means, and then the structure may be exposed to ultraviolet light, the ultraviolet light having an antimicrobial effect on the exterior surfaces of the couplers and the contaminated areas inside of the threaded conduits. After the structure has been exposed to ultraviolet light for a time sufficient to have an antimicrobial effect, the frangible means can be opened without reopening the coupler means, so that a closed system is maintained.

Specifically, the frangible means preventing flow may be a diaphragm positioned at the end of each coupler within each conduit, and spaced from the threads of the coupler and conduit for easy exposure at its outer surface to ultraviolet light passing through the valve means. Typically, spike means are positioned within the coupler, capable of being manually moved from the exterior to puncture the diaphragm after the antimicrobial exposure of ultraviolet light.

If desired, the coupler may be substantially opaque to ultraviolet light, thus being made of a less expensive material, since the interior portions of the coupler are sterilized at the factory. Thus, only the exterior portions of the coupler must receive the antimicrobial effects of the ultraviolet light in the process described herein.

It is desirable for the area of the conduit defining the threads of the conduit to be thinner than the area of the coupler defining the threads of the coupler means. This facilitates transmission of ultraviolet light into all nonsterile areas of the connected valve and coupler means, while at the same time the thicker portion of the threads of the coupler means provides sufficient mechanical strength for the device.

The spike may define a cut-away portion at its sharpened end, with the sharpened end defining a pointed edge at one side of the spike opposite the cut-away portion. As a result of this, the diaphragm is not cut away from the coupler interior wall at a certain area which is adjacent to the cut-away portion, and thus the diaphragm retains its attachment to the coupler interior wall. This prevents the diaphragm passing through the tubular system into the peritoneal cavity of the patient, or falling free to block flow at some point in the system.

Also, stop means are carried by the coupler means to prevent overadvancement of the coupler means into the conduits which, in turn, avoids stripping of the respective threads.

Furthermore, it is desirable for bellows means to be provided to permit longitudinal collapse of the coupler, which provides means for advancing the spike upon said collapse to penetrate the diaphragm after the antimicrobial effect of ultraviolet light on the immediate area of the connection.

The connector valve and conduits of this invention may be made of any substantially ultraviolet-transmissive material which has adequate stability in the presence of the intense ultraviolet radiation used herein to permit use for the desired period of time; the more transmissive the material is to ultraviolet light, the better. Preferably, connector valves and conduits may be made of a fluorocarbon material such as poly(trifluorochloroethane), for example, sold as KEL-F (by Minnesota Mining & Manufacturing), or other appropriate and stable fluorocarbon materials. The term "fluorocarbon materials" is not intended to exclude other chemical elements such as chlorine or hydrogen.

Alternatively, the connector valve and coupler means may be made of quartz, a highly transmissive material to ultraviolet radiation. Furthermore, silicone rubber, appropriately stabilized hydrocarbon resins, or other organic resins may be used as well.

The connector valve and adjacent connected conduits, after connection, may be placed into an ultraviolet light applicator to receive the antimicrobial effect of ultraviolet light. The applicator preferably comprises a casing, as well as means permitting placement of the connector valve into the casing.

The inner surfaces of the casing are preferably of an ultraviolet-reflecting material, to increase the intensity and maximize the incidence from multiple directions of the ultraviolet light on the connector valve and adjacent connected conduits.

An elongated ultraviolet light element is preferably positioned in the casing. The light element defines a plurality of convolutions, plus a channel between the convolutions of the element for receiving the connector valve. The convolutions of the ultraviolet light element are preferably positioned on at least three sides of the channel, extending substantially along the channel to be capable of irradiating transversely-disposed interior surfaces of the connector valve and connected conduits, such as the outer faces of the pierceable diaphragm and other transversely-disposed interior surfaces.

The ultraviolet light applicator preferably carries means for changing the various flow positions of a valve positioned in the applicator. Thus, the valve specifically described in this invention may be used to switch flow paths within the applicator without removing it from the field of exposure to ultraviolet light.

A predetermined overall exposure of ultraviolet radiation is preferably at least 600,000 microwatt-seconds/cm$^2$, specifically about 650,000 microwatt-seconds/cm$^2$, applied to assure maximum antimicrobial effect within the interior of the connector valve and adjacent conduits. The overall exposure time of course will be in part a function of the thickness and the ultraviolet transmissivity of the material used to make the multiple-way valve means and connected conduits.

Furthermore, in accordance with this antimicrobial connector invention, an inventive method is provided of draining spent peritoneal dialysis solution from the peritoneal cavity of a patient being treated by peritoneal dialysis, and then adding fresh peritoneal dialysis solution to the same cavity, in a manner that decreases the likelihood of transmitting microbial contamination to the peritoneal cavity of the patient. The method comprises the steps of:

(a) connecting a first access port of a first container filled with fresh peritoneal dialysis solution to a first connection port of a multiple-way valve means in communication with the patient's peritoneal cavity, said first access port and first connection port being both sealed at their inner ends to prevent migration of bacteria;

(b) connecting a second access port of an empty container to a second connection port of said multiple-way valve means in communication with the patient's peritoneal cavity, said second access port and second connection port being each sealed against migration of bacteria beyond a predetermined area, said predetermined area being spaced and sealed from the first access port and first connection port;

(c) flowing spent peritoneal dialysis solution from the patient's peritoneal cavity through said second connection port and second access port into said empty container while simultaneously exposing at least said first connection port and first access port to a sufficient quantity of ultraviolet radiation that an antimicrobial effect is obtained thereon;

(d) closing said second connection port; and (e) opening the seal between said first connection port and said first access port to flow fresh peritoneal dialysis solution from the first container into the patient's peritoneal cavity via said multiple-way valve means.

The first connection port is preferably sealed during the drain phase with an unbroken diaphragm, and also the valve means is preferably closed to the first connection port, to isolate any contaminated area from the flow path.

As the result of this, as spent peritoneal dialysis solution from the patient's peritoneal cavity is flowing into the empty container, a process that can take about 10 to 20 minutes, the first connection port is in the process of receiving the antimicrobial effect of ultraviolet radiation, so that when the drain phase has terminated, the spent, impurity-containing solution can be sealed in the formerly empty container, and the fresh dialysis solution can pass through the newly irradiated zone of connection, including the first connection port. Infusion of fresh dialysis solution occurs immediately after the drain phase, thus saving time.

The first and second access ports described in the method above may be provided by the conduits that communicate with the multiple-way valve means which is used to open and close the respective pathways of access, for example, the pathway of access of the spent dialysis solution after it has filled the empty container.

In one embodiment of the method of this invention, the empty container may be the initially-filled peritoneal dialysis solution container which was the source of the peritoneal dialysis solution administered to the patient. During the "dwell phase" of the peritoneal dialysis solution, amounting to several hours when the solution is in the patient, the patient is ambulatory, and may wear the flattened container under his clothes so that its connection is not disrupted. Accordingly, when the spent peritoneal dialysis solution flows from the patient's peritoneal cavity to the empty container it follows a previously irradiated path.

Just before the peritoneal dialysis solution is drained from the peritoneal cavity, a fresh container of peritoneal dialysis solution may be connected to another connection port of the multiple-way valve, and this connection will then not be sterile. However, this connection remains isolated from the remainder of the system by the fact that the multiple-way valve is closed to it, so that as the spent peritoneal dialysis solution flows it encounters a previously irradiated path. At the same time, the nonsterile areas of the multiple-way valve and conduits receive antimicrobial radiation during the same period of time by exposure to the ultraviolet light, after which the valve is opened to the fresh container.

It is generally preferred when sterility is breached at both the first and second connection ports by the fresh addition of the full bag and a new, empty bag, to have a prior irradiation period of all of the nonsterile connection areas before initiating the drain phase from the peritoneal cavity to the empty container.

BRIEF DESCRIPTION OF THE DRAWINGS

In the drawings,

FIG. 3 is an enlarged, longitudinal sectional view of a portion of the set of this invention, showing a threaded conduit in connection with the coupler means, prior to rupturing of the frangible diaphragm by the spike.

FIG. 4 is a similar longitudinal sectional view of the structure of FIG. 3, after rupturing of the diaphragm by means of the spike.

FIG. 5 is a fragmentary elevational view of part of an alternate set of this invention, taken partly in longitudinal section, showing the arrangement of the various convolutions of the elongated ultraviolet light element relative to the multiple-way valve and connected conduits when the multiple-way valve is positioned in the ultraviolet light applicator.

FIG. 6 is a plan view of the specific ultraviolet light element utilized in the embodiment of FIG. 5.

FIG. 7 is a view of the ultraviolet light element of FIG. 6, taken along line 7—7 of FIG. 6.

FIG. 8 is a view of the ultraviolet light element, taken along line 8—8 of FIG. 6.

FIG. 9 is a plan view of the ultraviolet light applicator utilized in this invention, containing one of the sets disclosed herein.

FIG. 10 is a front elevational view of the ultraviolet light applicator of FIG. 9.

FIG. 11 is a side elevational view of the ultraviolet light applicator of FIG. 9.

FIG. 12 is a detailed plan view, taken partly in longitudinal section, of the peritoneal dialysis set shown partially in FIG. 5, with some parts shown schematically.

FIG. 13 is a fragmentary, longitudinal sectional view of the multiple-way valve of the set of FIG. 12, taken along line 13—13 of FIG. 12.

DESCRIPTION OF THE PREFERRED EMBODIMENT

Figure 1:
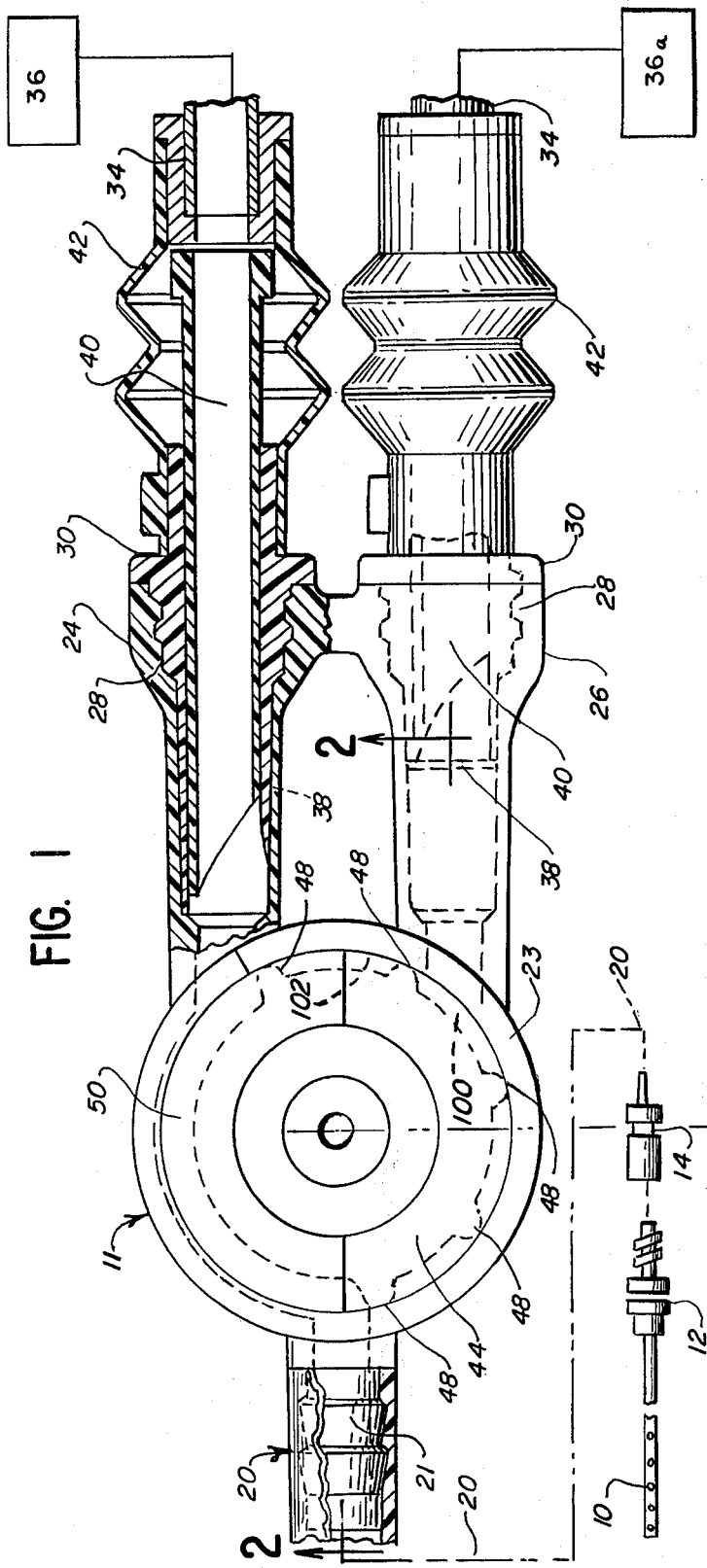
FIG. 1 is a detailed plan view, taken partly in longitudinal section, of a peritoneal dialysis set in accordance with this invention, with some portions thereof being shown schematically and in reduced scale.
Figure 2:
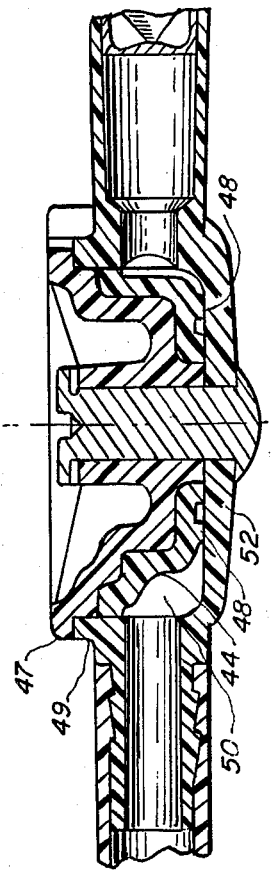
FIG. 2 is a fragmentary, longitudinal sectional view of the multiple-way valve of the set of FIG. 1.

Referring to FIGS. 1 and 2, a connector valve 11 is shown, being made in accordance with this invention to facilitate repeated connection and disconnection during peritoneal dialysis procedures, while substantially suppressing the risk of transmitting infectious bacteria into the peritoneal cavity.

Catheter 10 may be surgically implanted into the peritoneal cavity of the patient, with connector member 12 of conventional design being carried at an end thereof. Connector member 12 and catheter 10 may be constructed to be a generally permanent implant for the patient, with the connector 12 being preferably made of metal such as titanium for example, and catheter 10 being of durable silicone rubber for permanence and long life.

Tubing 20 permanently communicates with ultraviolet antimicrobial connector valve 11 as shown, with tubing 20 being sealed to port member 21, which may be an integral part of connector valve 11.

At the other end of tubing 20, a second connector 14 is provided, being optionally made of thermoplastic material and proportioned to form a sealed connection with connector member 12, which is carried at the end of catheter 10. Typically, connectors 12 and 14 may be of the design disclosed in Dennehey, et al. U.S. application Ser. No. 187,008, filed Sept. 15, 1980.

It is generally intended that tubing 20 and connector valve 11 will be connected to connector member 12 at a clinic or a hospital, with the connection operation being performed under aseptic conditions. Tubing 20 and connector valve 11 are then used on a frequent basis for a period of time, for example, about a month without disconnection of connector member 12 and second connector 14. Then, connectors 12, 14 are disconnected, once again at the clinic under aseptic conditions, and a fresh set comprising connector valve 11, tubing 20, and connector 14 are connected under the same aseptic conditions to connector member 12.

The relatively inexpensive set comprising tubing 20 and connector valve 11 may be subjected to ultraviolet radiation several times a day for a period of about a month, then being replaced before damage caused by the ultraviolet radiation to the material of connector valve 11 and other parts becomes excessive.

The ultraviolet radiation technique may be performed in the home by the patient or his family in the period between visits to the clinic when the connection between connector members 12 and 14 is made. This assures an antimicrobial connection with the bags of solution and drainage bags for frequent peritoneal dialysis solution exchanges after the user has been trained, without the need for the constant attention of a physician or a trained nurse.

As shown in the drawings, connector valve 11 comprises a housing 23, which may be made of a generally ultraviolet transmissive material such as KEL-F. Housing 23 further defines a pair of connector arms 24, 26 which may project outwardly from housing 23 at any desired angle, but preferably to form a parallel connection with tubing 20 as shown in FIGS. 1 and 2, a T connection as shown in FIGS. 12 and 13, or alternatively, a Y connection.

Connector arms 24, 26 each comprise generally rigid tubular structures defining a receptacle at their outer ends having helical female threads 28 proportioned to receive a penetrating coupler 30 which, in turn, defines projecting helical threads 32 to mate with threads 28 for sealing a penetrating coupler 30 to either connector arm 24 or 26. Each of penetrating couplers 30 is solvent sealed, heat sealed, or the like to flexible tubing 34, which may be made of polyvinyl chloride or the like. Tubing 34, in turn, may connect to a sealed container 36, 36a which may be of conventional design. As can be seen from FIG. 1, connector valve 11 is accordingly in flow connection through each of its connector arms 24, 26 to separate containers 36, 36a. One of the containers 36, 36a may serve as a source of peritoneal dialysis solution, while the other of the containers may be empty, and serves as a receptacle for spent peritoneal dialysis solution. For example, container 36a may be a collapsible bag which the patient can carry under his clothes, or alternatively, the patient can disconnect bags 36, 36a and cover the ports of connector valve 11 with protective caps.

Each of the penetrating couplers 30 has a diaphragm 38, preferably at its inner end, as shown. Freely movable, hollow spike member 40 is also provided in each of the coupler members 30. Hollow spike member 40 may be pushed inwardly by manual manipulation of plastic bellows portions 42 of tubing 34, to cause the pointed end of spike 40 to rupture diaphragm 38, when it is desired to open a connection between container 36 and connector 11.

Connector valve 11 defines a preferably elastomeric stopcock seal member 44, which is a rotatable member of generally circular structure, fitting within cylindrical housing 23 as part of connector valve 11, and carried by rotatable outer closure 47. Projections 48 provide hermetic sliding sealing contact between member 44 and housing 23.

Groove 50 is defined by one face of stopcock seal member 44, to rotate with the rotation of the seal member 44, to provide an on-off flow connection between tubing 20 and connector arms 24, 26. Accordingly, when diaphragm 38 is ruptured, peritoneal dialysis solution from container 36 can pass through groove 50 into tubing 20, and thus into catheter 10 and the peritoneal cavity of the patient, when seal member 44 is in the position as shown in FIG. 1. This can be used during the infusion phase of CAPD. Seal member 44 may then be rotated so that no flow can pass through the connector valve 11, for example, during the dwell phase of CAPD.

Thereafter, when it is desired to drain the spent peritoneal dialysis solution from the patient (CAPD drain phase), seal member 44 may be rotated so that groove 50 connects between tubing 20 and connector arm 26. The spike 40 of connector arm 26 may be advanced as in the previous manner to open a flow path between the patient's peritoneal cavity and the bag 36a connected therewith for receiving the drained peritoneal dialysis solution.

Thereafter, seal member 44 can be rotated again so that an additional portion of peritoneal dialysis solution may pass from a new bag 36 into the peritoneal cavity of the patient.

When it is desired to disconnect one or more of the penetrating couplers 30, seal member 44 is simply rotated to isolate the appropriate connector arm 24 and-/or 26 from groove 50, so that any contamination remains isolated in the respective connector arm upon opening.

As long as there is the possibility of the existence of contamination in either of connector arms 24, 26, seal member 44 should remain in a position to isolate that connector arm.

The structure of this invention may be then reconnected to a new projecting coupler 30 and its attached container 36 or 36a. Then, before seal member 44 is rotated, connector valve 11, including connector arms 24, 26, is exposed to an ultraviolet radiation source, preferably of a wavelength of about 254 nanometers, the antimicrobial wavelength of ultraviolet light, with the radiation passing through bottom wall 52 of housing 23 and other directions. An overall dosage of about 0.6 watt-sec/cm$^2$ or more may be provided for each irradiation with the ultraviolet radiation also passing through the projecting connector arm walls 24, 26. As stated above, these structures may comprise an integral piece, and they are made of a material having substantial transparency to the ultraviolet radiation used. As a result of this, the area within housing 23 and projecting arms 24, 26 are subjected to the antimicrobial effect of ultraviolet radiation including the outside surfaces of penetrating couplers 30.

It is preferred for the ultraviolet radiation to be applied to both the top and bottom of the connector valve 11, particularly in the area of the coupler members 30. If desired, tubing 20 may also be made of a material as described herein and exposed to ultraviolet radiation. Otherwise, it may be made of polyvinyl chloride or the like.

The exterior surfaces of diaphragms 38 should also receive the antimicrobial effect of ultraviolet radiation. To facilitate this, diaphragm 38 may be positioned at the outer end of coupler 30, so that all nonsterile surfaces are easily exposable to ultraviolet light. It is to be understood that the interior portions of coupler member 30 remain sterile as long as diaphragm 38 is not broken, so the couplers 30 do not have to made of an ultraviolet transparent material, although they may be so if desired.

Furthermore, groove 50 is exposed along its entire length to bottom wall 52 of housing 23, so it will receive antimicrobial radiation as well as the entire area inside of housing 23, although it is contemplated that contamination would not extend that far into the connector if proper procedure is used, because of the sealing areas 48.

Stopcock seal member 44 may, as shown in FIG. 2, comprise outer closure 47, attached to housing 23 by an interlocking flange structure 49 of conventional design, to provide a sealed but rotatable structure. Also, seal member 44 may be provided underneath closure 47, and attached thereto, being preferably made of silicone rubber to serve as a seal.

The connector members of this invention may be of any desired design, with the multiple-way valve connector structure as shown being only one particularly contemplated design. For example, luer-type connectors having flexible tubing that is pinched closed, with the ultraviolet radiation taking place after connection but before opening the pinch closures, constitutes another type of design in which the couplers of this invention may be used. Also, internal breakaway seals may be used of the general type shown in U.S. Pat. No. 4,181,140 in place of diaphragms 38.

Also, the connector of this invention may be utilized in procedures other than peritoneal dialysis, to facilitate the antimicrobial effect of ultraviolet radiation in other products and processes, such as parenteral solution administration in general and the like. Connector valves made with the materials as described in this invention may be reconnected and disconnected, with ultraviolet radiation providing repeated, reliable antimicrobial effect in the connector valve interior.

The ultraviolet irradiation may take place while spent peritoneal dialysis solution is flowing into bag 36a, to save time in the process, so that fresh peritoneal dialysis solution may pass from bag 36 into the patient's peritoneal cavity promptly after the drainage step. It is also desirable, but not necessary, for the ultraviolet irradiation to continue while the solution is passing from bag 36 into the patient's peritoneal cavity.

Referring to FIGS. 3 and 4, longitudinal sectional views of the connection between connector arm 26 and its associated coupler member 30 are shown, FIG. 3 showing spike 40 in its original configuration, and FIG. 4 showing spike 40 in its advanced configuration when a flow path is opened through the connector and coupler. The details of structure shown are typically similar to connector arm 24 and its associated coupler 30.

It is preferred for the area of connector arm 26 which defines internal threads 28 to be of less thickness than the area of coupler member 30 which defines the threads 32 of the coupler member, engaging threads 28. Accordingly, there is less thickness of material in coupler arm 26 than would otherwise be present, which facilitates the transmission of ultraviolet radiation to the junction 60 between the respective threads.

Spike member 40 may also define a cut-away portion 62 at its sharpened end 64, with the sharpened end 64 defining a pointed edge at one side of spike 40, as shown, which is opposed to cut-away portion 62. As the result of this, diaphragm 38 is not completely cut away from coupler means 30 as spike 40 is advanced as in FIG. 4, but retains its attachment to at least one position 66 so that the diaphragm 38 is not cut completely loose from the assembly.

An annular stop flange 68 is also defined on coupler 30, to prevent overadvancement of screw-threaded travel by the coupler, to prevent stripping of threads 28.

It should also be noted that, as an additional seal between coupler 30 and connector arm 26, coupler 30 defines a slightly tapered, tubular portion 70 to sealingly fit within connector arm 26 with a luer-type seal, to assure that no contamination can enter the system while coupler 30 and connector arm 26 are in engaged relation. Tubular portion 70 is axially spaced from screw threads 32 of the coupler member.

After connector arm 26 and coupler member 30 have been irradiated with ultraviolet light, the system may be opened by manually grasping sleeve 72 of coupler 30 and collapsing it into the configuration of FIG. 4. Spike 40 is advanced through diaphragm 38 by the pressure of annular seat 73 against enlarged end 74 of hollow spike 40. Spike 40 may be proportioned so that it slides through the bore of coupler member 30 with a measure of frictional resistance, so that it will be positively retained in any desired axial position, to prevent accidental withdrawal of the spike, which could release diaphragm 38 and allow it to occlude flow through the system.

Fin members 76 may be provided, for example four of such fins spaced 90° apart, as a gripping aid to aid in the coupling and uncoupling of members 26, 30.

Referring to FIGS. 5 through 13, details of how the structure of this invention mat be ultraviolet irradiated are shown. FIGS. 12 and 13 disclose details of another embodiment of peritoneal dialysis set in accordance with this invention, in which the reference numerals are identical with the reference numerals of FIGS. 1 and 2, and point to the corresponding and similar structures of FIGS. 12 and 13. The set of FIGS. 12 and 13 functions in a manner which is similar to the functioning of the set of FIGS. 1 and 2 as previously described, with the exception that the connector arms 24, 26 in FIGS. 12 and 13 are opposed to each other rather than parallel as in FIGS. 1 and 2.

FIGS. 5 through 11 show details of the ultraviolet irradiation apparatus which is adapted for use in conjunction with the set of FIGS. 12 and 13.

In FIG. 5, connector valve 11 is shown with connector arms 24, 26 being attached to coupler members 30. Valve 11 and connected structures are positioned in an ultraviolet light applicator or "box" as disclosed in FIGS. 9 through 11. The applicator includes a casing 80, shown in phantom in FIG. 5. Hinged hatch means 82 permits placement of the connector valve 11 and the attached arms of conduits 24, 26 into the housing 80. The inner surface of housing 80 may be of an ultraviolet-reflecting material 84, for example, an etched aluminum coating to maximize the exposure of ultraviolet light by the contents of the applicator.

In accordance with this invention, an elongated ultraviolet light element 86 is provided in the housing 80, defining a plurality of convolutions 88 through 92. The convolutions 88 through 92 are positioned to define a channel 94 which is proportioned for receiving connector valve 11 and connector arms 26, 28 with the convolutions 88 through 92 being positioned on at least three sides of the channel, and extending substantially along the channel so that ultraviolet light is propagated from a continuum of positions along the channel. Thus, the ultraviolet light source is capable of irradiating the transversely disposed interior surfaces of the system, for example, the outer surface of each of diaphragms 38, prior to rupturing, with at least a portion of ultraviolet source 86 defining an angle to the plane of each diaphragm 38 of about 20° to 60°, for direct irradiation thereof.

Because ultraviolet light element 86 is elongated and propagates its ultraviolet light from a continuum of sources, there can be no nooks or crannies capable of contact with the liquid flow paths inside of valve 11 or connector arms 24, 26 which are unexposed to the ultraviolet light.

Particularly, convolution 91 of the ultraviolet light element is positioned to irradiate ultraviolet light onto the outer, nonsterile surface of membrane 38, on the opposite side from the corresponding spike member 40 in arm 26. Convolution 89 is similarly positioned for the irradiation of the other diaphragm 38 positioned by coupler 30 into connector arm 28 prior to rupture by spike 40. These convolutions also irradiate bottom wall 52 of connector valve 11.

Convolutions 88 and 92 irradiate the tops of coupler arms 24, 26, so that at least the great majority of the sealed connection between each coupler member and connector arms 26, 28 is irradiated. Convolution 90 provides additional lateral ultraviolet irradiation, while the ultraviolet radiation propagated from all of the element 86 is reflected off the housing walls 80 of the applicator back to the valve 11 from a multitude of angles and directions, for complete irradiation of the interior portions thereof.

Control knob 96 is provided, communicating with interlocking projection 98 of interlocking housing portion 47, so that seal member 44, which is attached to housing portion 47, may be rotated by rotation of the control knob 96 to control the position of flow channel 50; the control knob 96 may be permanently attached to the box or detachable from the box. As shown in FIG. 5, flow channel 50 is directly exposed to ultraviolet transmission through bottom wall 52 for sterilization of the internal portions of channel 50.

Ultraviolet light element 86 is preferably of a generally h-shape when viewed along a dimension as shown in FIG. 8, and it also may be generally of a w-shape when viewed along the dimension as shown in FIG. 7.

While preferably five specific convolutions are used in the specific ultraviolet element 86 illustrated herein, ultraviolet elements having more or less than five convolutions may also be utilized in this invention to obtain a large, multi-dimensional continuum of sources of ultraviolet radiation for having an antimicrobial effect on the connector system.

It is also preferred for a photocell 87 to be provided within housing 80 to measure the total energy of ultraviolet light applied in each sterilization procedure. When the total energy reaches the predetermined overall desired exposure level, for example 0.6 watt·sec/cm$^2$, the photocell means activates a transducer connected to the photocell to shut off the ultraviolet light element. Accordingly, the sterilizing process of this invention does not have to use a timing sequence or the like, which can be inaccurate since ultraviolet elements can significantly change the intensity of their propagation of ultraviolet radiation. Instead, the applicator can operate until the predetermined total energy of ultraviolet exposure is emitted, following which the apparatus is activated to shut off.

Accordingly, connector valve 11 with its arms 21, 24, 26 may be placed into housing 80 for ultraviolet irradiation, with each of connector arms 24, 26 being connected to a coupler 30 which, in turn, connects to bags 36, 36a in aseptic manner.

In the use of the device of this invention, as previously described, tubing 20 communicates with connector valve 11. Tubing 20 terminates with coupler 14, which is aseptically connected to coupler 12 of implanted catheter 10. After connection with a coupler 30 and bag 36 to arm 24 and after ultraviolet irradiation has appropriately proceeded, spike 40 within arm 24 is advanced to rupture the associated membrane 38, and the peritoneal dialysis solution of container 36 is transferred to the peritoneal cavity by passage through channel 50, tube 20 and catheter 10.

Sealing member 44 may then be rotated so that channel 50 communicates with no conduit, to seal off all of the conduits.

If desired, bag 36 may be retained under the clothes during the dwell phase of the peritoneal dialysis solution in the peritoneal cavity. The other arm 26 is typically sealed under this circumstance and free of connection with a coupler 30. Thus, the patient is free to go about normal daily activities, with connector valve 11 and the flat bag 36 worn under his or her clothes.

At the termination of the several hour dwell phase for the peritoneal dialysis solution, the patient is free to go about normal daily activities, with connector valve 11 and the flat bag 36 worn under his or her clothes.

At the termination of the several hour dwell phase for the peritoneal dialysis solution, the patient can remove connector valve 11 and bag 36 from under his or her clothes, connect a coupler and bag 36a of fresh solution to arm 26, and insert the connector valve 11 once again into housing 80 for ultraviolet irradiation. Sealing member 44 can be moved, controlled by knob 98, once again so that channel 50 communicates between tubing 20 and arm 24, with the result that spent peritoneal dialysis solution flows from the peritoneal cavity back to bag 36, while the ultraviolet element 86 in housing 80 irradiates the entire connector valve 11 and arms 24, 26. The path of flow remains closed, if proper procedure has been used, so that channel 50 has not been exposed to the passageway inside of arm 26, with a barrier being produced by sealing projections 48 against the interior of casing 23. Thus, any nonsterile contamination remains isolated, for example in area 100 (FIG. 12).

During the time of outflow of peritoneal dialysis solution into bag 36 along its closed pathway, the ultraviolet radiation passing into the interior of valve 11, including arms 24, 26, provides an antimicrobial effect on the enclosed areas therein, including area 100 and any other pockets of contamination that may exist, for example area 102 resulting from the rotation of seal member 44, prior to which rotation area 102 communicated with arm 26.

At the termination of the drainage and ultraviolet radiation step, knob 98 is turned to rotate seal member 44 so that channel 50 communicates between connector arm 26 and tubing 20, with the result that fresh peritoneal dialysis solution from bag 36a can flow into the patient's peritoneal cavity. At the same time the flow connection between bag 36 and the peritoneal cavity is terminated with the seal provided by seal member 44.

After the contents of bag 36a have drained into the patient's peritoneal cavity, bag 36 and its associated coupler 30 may be removed which, of course, exposes the interior of arm 24 to potential contamination. However, the contamination is limited by the position of seal 44, so that it can only find its way into one or two of the pockets analogous to pockets 100, 102, which remain isolated from the then flow path communicating with the peritoneal cavity.

Following this, without further rotation of sealing member 44, connector valve 11 may be removed from the ultraviolet applicator, and flat bag 36a and connector valve 11 may be placed under the clothes of the patient, for him to resume his normal activities until it is time to repeat the process, utilizing bag 36a as the drainage bag. A new bag 36 and coupler 30 may be attached to arm 24, followed preferably by drainage from the peritoneal cavity into bag 36a simultaneously with irradiation of the system as before, so that the flow path between new bag 36 and the peritoneal cavity may be irradiated by ultraviolet light prior to its use.

Alternatively, after placement of the peritoneal dialysis solution into the peritoneal cavity, one may remove both bags 36, 36a and their couplers 30, after turning seal member 44 to a position that prevents flow through and seals all of its flow paths. In this instance, when it is desired to change the peritoneal dialysis solution, one connects new pairs of bags 36, 36a, with their respective couplers, placing connector valve 11 into ultraviolet applicator housing 80 for typically a ten minute application of ultraviolet radiation *prior to* moving seal member 44 into a connecting position with a passageway for drainage of the peritoneal dialysis solution.

The above has been offered for illustrative purposes only, and is not intended to limit the scope of the inven- That which is claimed is:

1. A connector valve for selectively permitting the transfer of fluids therethrough, which comprises multiple-way valve means communicating with a plurality of conduits and selectively permitting and preventing flow between the conduits; said multiple-way valve means comprising outer walls made of substantially ultraviolet-transmissive material; said outer walls of the multiple-way valve means enclosing an elastomeric seal member, said seal member defining rotatable flow channel means for communication with differing conduits at differing rotational positions and providing rotatable seal means against inner surfaces of said outer walls to maintain antimicrobial conditions within said valve, said flow channel means being exposed along its entire length to an inner surface of an outer wall, and means for relatively rotating said seal member relative to said conduits.

2. The connector valve of claim 1 in which at least two of said conduits carry at their ends threaded means for receiving and fixedly retaining couplers for connection to fluid containers.

3. The connector valve and coupler means of claim 1 in which the outer walls are made of quartz.

4. The connector valve and coupler means of claim 1 in which the outer walls are made of a fluorocarbon material.

5. A connector valve for selectively permitting the transfer of fluids therethrough, which comprises multiple-way valve means communicating with a plurality of conduits and selectively permitting and preventing flow between said conduits, said multiple-way valve means comprising outer walls made of substantially ultraviolet-transmissive material, said outer walls of the multiple-way valve means enclosing rotatable flow channel defining means for communicating with differing rotational positions and providing rotatable seal means against inner surfaces of said outer walls to maintain antimicrobial conditions within said valve, the flow channel defined by the flow channel defining means being exposed along its entire length to an inner surface of an outer wall, and means for rotating said seal member relative to said conduits, at least one of said conduits carrying at its end threaded means for receiving and fixedly retaining coupler means connected to fluid containers; said coupler means being threadedly and in sealingly interlocked relation with said conduits, said coupler means projecting into said threaded conduits and defining frangible means preventing flow through said coupler means, said frangible means being openable to permit flow without disconnection from said conduits, the exposed, outer surfaces of said coupler means positioned within said conduits being positioned for exposure to ultraviolet light passing through said valve means, said frangible means preventing flow being a diaphragm positioned at the end of said coupler means within each conduit and spaced from the threads of said coupler means and conduits for easy exposure of its outer surface to ultraviolet light passing through said valve means, and spike means positioned within said coupler means capable of being manually moved from the exterior to puncture said diaphragm after exposure to a sufficient quantity of ultraviolet light to have maximum antimicrobial effect.

6. The connector valve and coupler means of claim 5 in which one conduit is free of said threaded means and is in flow communication with an indwelling peritoneal catheter of a patient.

7. The connector valve and coupler means of claim 5 in which said coupler means is substantially opaque to ultraviolet light.

8. The connector valve and coupler means of claim 5 in which the wall defining threads of said conduit is thinner than the wall defining threads of the coupler means.

9. The connector valve and coupler means of claim 5 in which said spike defines a cut-away portion at its sharpened end, said sharpened end defining a pointed edge at one side of the spike opposed to said cut-away portion, whereby the diaphragm is not cut away from the coupler means at the area adjacent the cut-away portion and retains its attachment thereto.

10. The connector valve and coupler means of claim 5 in which stop means are carried by said coupler means to prevent overadvancement of the coupler means into said conduits and stripping the respective threads.

11. The connector valve and coupler means of claim 5 in which said coupler means defines bellows means for longitudinal collapse of said coupler means and means for advancing said spike upon said collapse.

12. The connector valve and coupler means of claim 5 in which said flow channel defining means includes an elastomeric seal member defining said rotatable flow channel means.

13. A connector valve for selectively permitting the transfer of fluids therethrough, which comprises multiple-way valve means communicating with a plurality of conduits and selectively permitting and preventing flow between said conduits, said multiple-way valve means comprising outer walls made of a substantially ultraviolet transmissive material, at least two of said conduits removably receiving couplers connected with fluid containers, and means for fixedly but removably retaining said couplers in communication with said conduits, each of said couplers carrying frangible means preventing flow through said couplers, said frangible means being openable to permit fluid flow without disconnection from said conduits, the outer surfaces of said couplers positioned within the conduits to receive antimicrobial irradiation by ultraviolet light passing through said valve means, said frangible means preventing flow being a diaphragm positioned at the end of said couplers within each conduit for exposure of its outer surface to ultraviolet light passing through said valve means for antimicrobial irradiation, and spike means positioned within said couplers capable of being manually moved from the exterior to puncture said diaphragm after irradiation.

14. The connector valve and couplers of claim 13 in which each conduit is capable of receiving a coupler means, and each coupler means, is tapered to provide a luer-type seal, said conduit and coupler means each defining removably interengaged threads for retention with each other.

15. The connector valve and couplers of claim 14 in which one conduit is free of said threaded means and is in flow communication with an indwelling peritoneal catheter of a patient.

16. The connector valve and couplers of claim 14 in which the area defining threads of said conduit is thinner than the area defining threads of the coupler means.

17. The connector valve and couplers of claim 14 in which said spike defines a cut-away portion at its sharpened end, said sharpened end defining a pointed edge at one side of the spike opposite to said cut-away portion, whereby the diaphragm is not cut away from the coupler means when the spike punctures the diaphragm.

18. The connector valve and couplers of claim 14 in which stop means are carried by said coupler means to prevent overadvancement of the coupler means into said conduits and stripping of the respective threads.

19. The connector valve and couplers of claim 14 in which said couplers define bellows means carried thereon for longitudinal collapse of said couplers; and means for advancing said spike upon said collapse to penetrate the diaphragm.

20. A connector valve for selectively permitting the transfer of fluids therethrough, which comprises multiple-way valve means communicating with a plurality of conduits and selectively permitting and preventing flow between said conduits, said multiple-way valve means comprising outer walls made of substantially ultraviolet-transmissive material, said outer walls of the multiple-way valve means enclosing rotatable flow channel defining means for communicating with differing rotational positions and providing rotatable seal means against inner surfaces of said outer walls to maintain antimicrobial conditions within said valve, the flow channel defined by the flow channel defining means being exposed along its entire length to an inner surface of an outer wall, and means for rotating said seal member relative to said conduits, at least one of said conduits carrying at its end threaded means for receiving and fixedly retaining coupler means connected to fluid containers; said coupler means being threadedly and in sealingly interlocked relation with said conduits, said coupler means projecting into said threaded conduits and defining frangible means preventing flow through said coupler means, said frangible means being openable to permit flow without disconnection from said conduits, the exposed, outer surfaces of said coupler means positioned within said conduits being positioned for exposure to ultraviolet light passing through said valve means.

21. The method of performing peritoneal dialysis by draining spent peritoneal dialysis solution from, and then adding fresh peritoneal dialysis solution to, the peritoneal cavity of a patient being treated by peritoneal dialysis in a manner that decreases the likelihood of transmitting microbial comtamination to the peritoneal cavity of the patient, the method comprising the steps of:
(a) connecting a first access port of a first container filled with fresh peritoneal dialysis solution to a first connection port of a multiple-way valve means in communication with the patient's peritoneal cavity, said first access port and first connection port being both sealed at their inner ends to prevent migration of bacteria in the direction of the peritoneal cavity;
(b) connecting a second access port of an empty container to a second connection port of said multiple-way valve means in communication with the patient's peritoneal cavity, said second access port and second connection port being each sealed against migration of bacteria in the direction of the peritoneal cavity beyond a predetermined area, said predetermined area being spaced and sealed from the first access port and first connection port;
(c) flowing spent peritoneal dialysis solution from the patient's peritoneal cavity through said second connection port and second access port into said empty container while simultaneously exposing at least said first connection port and first access port to a sufficient quantity of ultraviolet radiation that an antimicrobial effect is obtained thereon;
(d) closing said second connection port; and then
(e) opening the seal between said first connection port and said first access port to flow fresh peritoneal dialysis solution from the first container into the patient's peritoneal cavity via said multiple-way valve means.

22. The method of claim 21 in which said multiple-way valve means comprise outer walls made of a substantially ultraviolet-transmissive material and defining flow channel means through said multiple-way valve means which are exposed along the entire length thereof to an inner surface of an outer wall.

23. The method of claim 22 in which each container which is emptied as the peritoneal dialysis solution passes into the peritoneal cavity of the patient is retained in seal relation to a connection port of said conduit until the peritoneal dialysis solution is once again drained from the patient's peritoneal cavity to said container.

24. The method of claim 22 in which, after peritoneal dialysis solution flows from said first container to the peritoneal cavity of a patient, the connection ports of said multiple-way valve means connected to said containers are sealed and said containers removed, and thereafter an empty container is attached to a connection port of said conduit, and the connection port is exposed to a sufficient quantity of ultraviolet radiation so that an antimicrobial effect is obtained upon said connection port, the seal of said connection port being then removed to permit spent peritoneal dialysis solution to flow from the patient's peritoneal cavity to said newly attached container.

25. The method of performing peritoneal dialysis by draining spent peritoneal dialysis solution from, and then adding fresh peritoneal dialysis solution to, the peritoneal cavity of a patient being treated by peritoneal dialysis in a manner that decreases the likelihood of transmitting microbial contamination to the peritoneal cavity of the patient, the method comprising the steps of:
(a) connecting an access port of a first container filled with fresh peritoneal dialysis solution to a first connection port of a conduit in communication with the patient's peritoneal cavity, said access port and first connection port being both sealed at their inner ends to prevent migration of bacteria in the direction of the peritoneal cavity;
(b) exposing said first connection port and first access port to a sufficient quantity of ultraviolet radiation so that an antimicrobial effect is obtained thereon;
(c) opening the seals between said access port and connection port to allow peritoneal dialysis solution to flow from the first container to the patient's peritoneal cavity;
(d) connecting a second container filled with fresh peritoneal dialysis solution to a second connection port of a conduit in communication with the patient's peritoneal cavity, said second access port and connection port being each sealed against migration of bacteria in the direction of the peritoneal cavity beyond a predetermined area, said predetermined area being spaced and sealed from the first access port and connection port;

(e) flowing spent peritoneal dialysis solution from the patient's peritoneal cavity through said first connection port and access port into said empty container while simultaneously exposing at least said second connection port and access port to a sufficient quantity of ultraviolet radiation that an antimicrobial effect is obtained thereon;

(f) closing at least said first connection port; and then (g) opening the seal between said second connection port and said second access port to flow fresh peritoneal dialysis solution from the second container into the patient's peritoneal cavity via said conduit, in which said first and second connection ports constitute part of multiple-way valve means for selectively opening and sealingly closing off flow communicating between said first and second connection ports and the conduit in communication with the patient's peritoneal cavity, said multiple-way valve means comprising outer walls made of a substantially ultraviolet-transmissive material and defining flow channel means through said multiple-way valve means, said flow channel means being exposed along the entire length thereof to an inner surface of an outer wall.

26. The method of claim 25 in which each container which is emptied as the peritoneal dialysis solution passes into the peritoneal cavity of the patient is retained in sealed relation to a connection port of said conduit until the peritoneal dialysis solution is once again drained from the patient's peritoneal cavity to said container.

27. The method of claim 25 in which, after peritoneal dialysis solution flows from said first and second containers to the peritoneal cavity of a patient, the connection port of said conduit connected to said container is sealed and said container removed, and thereafter an empty container is newly attached to a connection port of said conduit, and the connection port is exposed to a sufficient quantity of ultraviolet radiation so that an antimicrobial effect is obtained upon said connection port, the seal of said connection port being then removed to permit spent peritoneal dialysis solution to flow from the patient's peritoneal cavity to said newly attached container.

28. A connector member for providing substantially aseptic connection between a peritoneal tube for connection with the peritoneal cavity of a patient and a dialysis solution container port tube, which connector member comprises:

a first coupler on one end of said peritoneal tube, a second coupler on the outer end of said container port tube, said first and second couplers being proportioned for sealing connection in telescoping relation while permitting fluid flow between the peritoneal tube and container port tube, the innermost of said couplers in telescoping relation being sealed at its outer end with a diaphragm, a spike member, one of said couplers surrounding said spike member, means for rendering said spike member manually advanceable to penetrate said diaphragm while the couplers are connected, said first and second couplers each defining mating screw threads for connection therebetween, said couplers each also defining, at portions axially spaced from said screw threads, tapered, tubular portions proportioned to sealingly fit together in telescoping relation, when the couplers are connected together, to form a luer-type seal, at least the coupler defining the outermost of said tapered, tubular portions in said telescoping relation being made of a material and a thickness to permit the substantial transmission of ultraviolet radiation from the exterior to the interior thereof for antibacterial effect in areas possibly exposed to contamination during the connection process.

29. The connector member of claim 28 in which bellows means are provided to facilitate manual penetration of the spike member through the diaphragm.

30. The connector member of claim 29 in which both tapered, tubular portions are made of ultraviolet transparent material to permit substantial transmission of ultraviolet radiation therethrough.

31. A coupler member for connecting one tube end with another by a connection with another mating coupler, said coupler member being carried on flow conduit means for medical solution for communication with a medical solution container, said coupler member defining a tubular body having screw threads for mating closure with the other coupler, and a tapered tubular portion axially spaced from said screw threads for sealing fit with a corresponding tapered tubular portion of the other coupler in a luer-type seal, said coupler being made of a material and a thickness to permit the substantial transmission of ultraviolet radiation from the exterior to the interior thereof.

32. The coupler member of claim 31 which surrounds a spike member and defines an outer end, and a diaphragm carried at said outer end.

33. The coupler member of claim 32 including a flexible bellows member carried thereon in which said flexible bellows member is provided to permit manual advancement of a spike member through the diaphragm.

34. The coupler member of claim 31 having an outer end, said tapered tubular portion axially spaced from the screw threads being positioned adjacent said outer end, said outer end being closed by a puncturable diaphragm.

* * * * *